United States Patent [19]

Tanaka

[11] Patent Number: 5,680,865
[45] Date of Patent: Oct. 28, 1997

[54] DUAL ULTRASOUND PROBE

[75] Inventor: Toshizumi Tanaka, Omiya, Japan

[73] Assignee: Fuji Photo Optical Co., Ltd., Omiya, Japan

[21] Appl. No.: 544,473

[22] Filed: Oct. 18, 1995

[30] Foreign Application Priority Data

Oct. 20, 1994 [JP] Japan .................................. 6-279825

[51] Int. Cl.$^6$ .......................................................... A61B 8/06
[52] U.S. Cl. ............................. 128/660.05; 128/662.06
[58] Field of Search ........................ 128/660.04, 660.05, 128/661.09, 661.1, 662.04

[56] References Cited

U.S. PATENT DOCUMENTS

| | | | |
|---|---|---|---|
| 4,097,835 | 6/1978 | Green | 128/660.05 |
| 4,228,687 | 10/1980 | Fraser | 128/660.05 |
| 4,407,293 | 10/1983 | Surez, Jr. et al. | 128/660.05 |
| 4,476,874 | 10/1984 | Taenzer et al. | 128/660.05 |
| 4,501,277 | 2/1985 | Hongo | 128/661.09 X |
| 4,622,978 | 11/1986 | Matsuo et al. | 128/660.05 |
| 4,850,362 | 7/1989 | Rello et al. | 128/660.05 |
| 4,893,628 | 1/1990 | Angelsen | 128/660.05 |
| 5,131,393 | 7/1992 | Ishiguro | 128/662.06 |
| 5,131,396 | 7/1992 | Ishiguro | 128/662.06 |
| 5,150,715 | 9/1992 | Ishiguro | 128/662.06 |
| 5,211,176 | 5/1993 | Ishiguro | 128/662.06 |
| 5,257,628 | 11/1993 | Ishiguro | 128/660.06 |

*Primary Examiner*—Francis Jaworski
*Attorney, Agent, or Firm*—Oblon, Spivak, McClelland, Maier & Neustadt, P.C.

[57] ABSTRACT

A dual ultrasound probe which incorporates, in combination with a B-mode ultrasound scanner capable of scanning an intracorporeal region of interest over a predetermined scanning range to display a B-mode tomographic ultrasound image of the scanned region on a monitor screen, a Doppler ultrasound observation means capable of shifting its position of observation substantially throughout the scanning range of the B-mode ultrasound scanner to check for in vivo motional conditions, for example, for blood flows at an echoless blank spot in a B-mode ultrasound image on display on the monitor screen.

3 Claims, 8 Drawing Sheets

F I G. 2
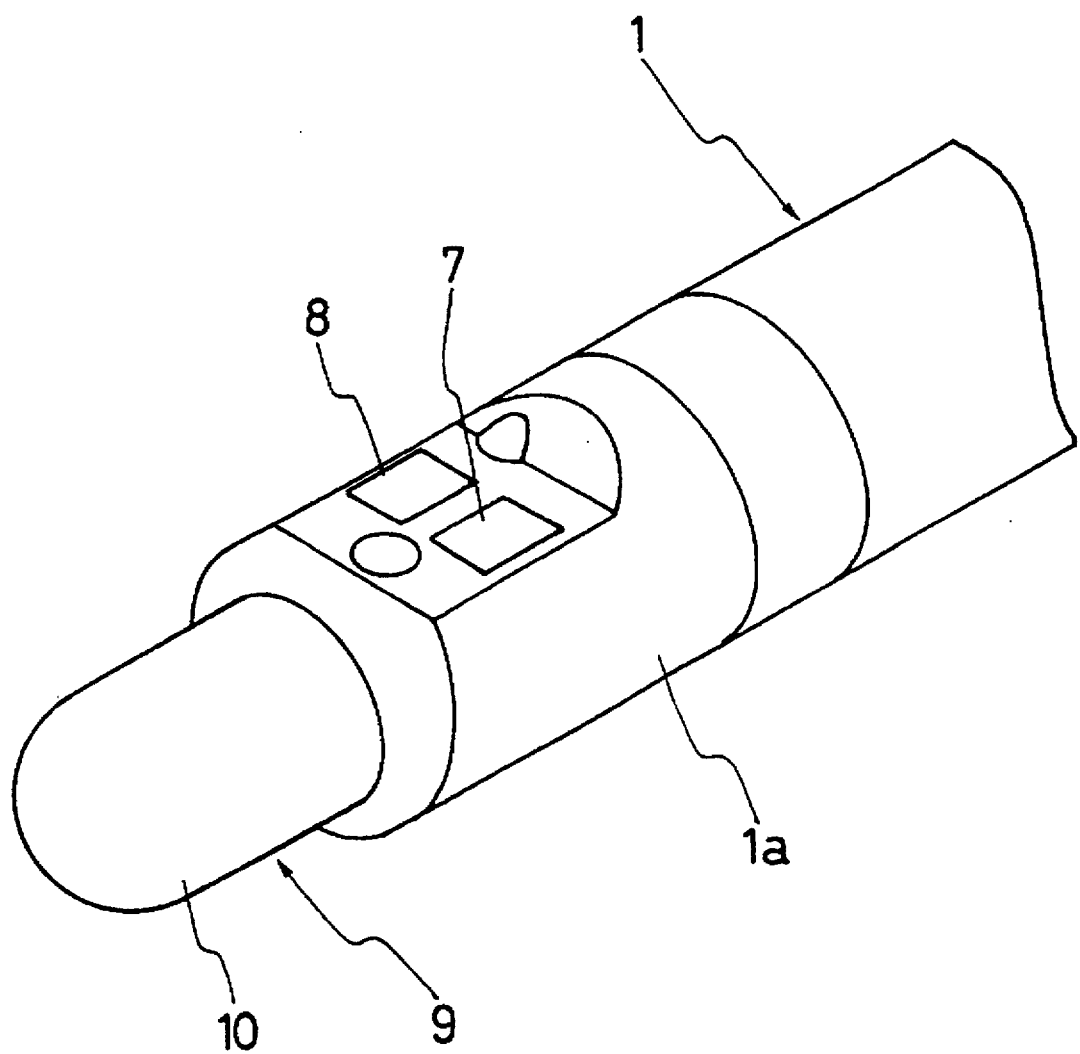

DUAL ULTRASOUND PROBE

BACKGROUND OF THE INVENTION

1. Field of the Art

This invention relates to an ultrasound probe suitable for use in medical ultrasound examination systems, and more particularly to a dual ultrasound probe which incorporates a Doppler ultrasound observation means in combination with a B-mode ultrasound scanner capable of producing B-mode tomographic ultrasound images, enabling the operator to obtain information on in vivo motions at a specific spot of a B-mode tomographic ultrasound image under observation through the B-mode scanner.

2. Prior Art

As well known in the art, in addition to ultrasound probes with an A-mode, B-mode or M-mode scanning system, there have been in use the so-called Doppler ultrasound probes which are capable of detecting blood flows or other in vivo motions. For instance, in case of an ultrasound probe with a B-mode scanning system, an intracorporeal portion of interest is scanned with an ultrasound transducer means mechanically or electronically over a certain scanning range to display on a monitor screen a tomographio ultrasound image which contains information of tissues in the scanned direction. Depending upon the scanning direction of the ultrasound transducer means, the B-mode scanning operation is referred to as a linear scan (driving a transducer linearly in an axial direction of a probe), a radial scan (driving a transducer rotationally about an axis of a probe), a sectoral scan (scanning a particular sector in a rotational direction), or a convex scan.

Irrespective of the type of drive, which may be mechanical or electronic, or the scanning direction of the ultrasound transducer, the tomographic ultrasound images which are displayed on a monitor screen are produced on the basis of reflected ultrasound echoes from tissue portions with different characteristics in acoustic impedance. Accordingly, distinctive echo signals cannot be received from a homogeneous medium which has an even acoustic impedance as in the case of blood vessels or lymph glands which convey a flow of blood or lymph. Therefore, in B-mode ultrasound scanning operations, such portions appear simply as echoless blank areas in tomographic ultrasound images which are displayed on a monitor screen, without giving any clear information as to the nature of such blank areas. Namely, on the basis of B-mode tomographic ultrasound images alone, it is difficult to determine whether such echoless blank areas indicate a blood vessel or a diseased portion. When scanning a region containing a previously spotted diseased portion such as cancer cells, for example, it would be a great help in giving an appropriate diagnostic judgement if one can confirm existence of a blood flow in that region by observation of displayed ultrasound images. However, it is difficult to obtain all of necessary information by B-mode ultrasound scanning operations.

In case of a Doppler ultrasound probe which operates on the principles that, when an ultrasound beam is transmitted into a blood flow or other in vivo motional medium, a shift in frequency occurs to return echo signals from blood cells in the blood flow in such a way as to indicate existence of a blood flow and its velocity. Therefore, a Doppler ultrasound probe can provide information concerning blood flows in a scanned intracorporeal region. However, to the best of the inventor's knowledge, no one has ever succeeded in developing an ultrasound probe system which incorporates a Doppler ultrasound observation means operatively in combination with a B-mode ultrasound scanner, to permit the operator to detect in vivo motional conditions at a particular spot of a tomographic ultrasound image as obtained by the use of a B-mode ultrasound scanner.

SUMMARY OF THE INVENTION

In view of the situations as explained above, the present invention has as its object the provision of a dual ultrasound probe for use in an ultrasound examination system, the dual ultrasound probe incorporating a Doppler ultrasound observation means operatively in combination with a B-mode ultrasound scanner to provide information concerning in vivo motional conditions such as blood flows at a specified spot of a tomographic ultrasound image displayed on a monitor screen by operation of the B-mode ultrasound scanner.

In accordance with the present invention, the above-mentioned objective is achieved by the provision of a dual ultrasound probe for use in an ultrasound examination system, which essentially includes: a B-mode ultrasound scanner having a scanning ultrasound transducer housed and supported in a probe head casing externally operably to make a B-mode ultrasound scan over a predetermined scanning range through an intracorporeal region of interest and to display a B-mode tomographio ultrasound image of the scanned region on a monitor screen; and a Doppler ultrasound observation means having a Doppler ultrasound transducer movably supported within the probe head casing together with the scanning ultrasound transducer externally operably to shift a position of Doppler observation substantially through the entire scanning range of the B-mode scanner for detecting in vivo motional conditions in a specified target spot of the B-mode tomographic ultrasound image on display on the monitor screen.

In a preferred form of the invention, the B-mode ultrasound scanner includes a B-mode drive means for mechanically or electronically driving the scanning ultrasound transducer through the scanning range, a position detection means for detecting a position of the scanning ultrasound transducer within the probe head casing, and a B-mode signal processor connected to the scanning ultrasound transducer through the B-mode drive means to process return echo signals from the scanning transducer into video signals for generation of the B-mode tomographic ultrasound image to be displayed on the monitor screen, and the Doppler ultrasound observation means comprises a Doppler positioning means for locating the Doppler ultrasound transducer at a target position in line with a target spot in the B-mode tomographic ultrasound image on display for transmission of a Doppler sampling signal and reception of return echo signals thereat, a Doppler position indicator adapted to detect a position of the Doppler ultrasound transducer and to indicate the position of the Doppler ultrasound transducer on the monitor screen in relation with the B-mode tomographic ultrasound image, and a Doppler signal processor for sampling return echo signals received through the Doppler transducer to check for in vivo motional conditions at the target spot in the B-mode tomographic ultrasound image on display on the monitor screen.

The above-mentioned Doppler transducer drive means may employ an electric motor for driving the Doppler ultrasound transducer into the target position in line with the target spot in the B-mode tomographic ultrasound image on display, and the Doppler position indicator may be arranged to indicate the target position of the Doppler transducer on the monitor screen. The above-mentioned drive motor is preferably connected to a drive control means for automatically advancing the Doppler ultrasound transducer to the target position as pointed by the Doppler position indicator.

Alternatively, the Doppler transducer drive means may employ a manual drive means for moving the Doppler ultrasound transducer to the target position, in association with the Doppler position indicator which is in this case arranged to indicate a current position of the Doppler ultrasound transducer on the monitor screen in relation with the B-mode tomographic ultrasound image on display.

The B-mode ultrasound scanner is started at a predetermined position in the usual manner, scanning an intracorporeal region of interest over a predetermined range while obtaining signals of a tomographic ultrasound image of the scanned region for display on a monitor screen. Whenever it becomes necessary to acquire motional information in a particular spot in the B-mode tomographic ultrasound image on display, the position of observation by the Doppler observation means is shifted to a position suitable for targeting at the spot to be checked for information on in vivo motional conditions.

Blood flows and lymph flows are typical examples of in vivo motional phenomena which are detectible by a Doppler ultrasound detector, but not by way of B-mode tomographic ultrasound images where blood and lymph flows appear as blank areas due to homogeneousness in acoustic impedance as mentioned hereinbefore. Therefore, the combination of the above-mentioned Doppler ultrasound observation means with a B-mode ultrasound scanner has a great significance in ultrasound examinations or from a diagnostic point of view, because it permits the operator to obtain information on in vivo motions such as blood flows at an echoless ambiguous spot in a B-mode tomographic ultrasound image which is being displayed by operation of the B-mode ultrasound scanner.

The above and other objects, features and advantages of the invention will become apparent from the following particular description of the invention, taken in conjunction with the accompanying drawings which show by way of example some preferred embodiments of the invention.

BRIEF DESCRIPTION OF THE DRAWINGS

In the accompanying drawing:

FIG. 2 is a schematic outer view of a fore end portion of an insertion tube of an endoscope-ultrasound probe assembly unit;

PARTICULAR DESCRIPTION OF THE INVENTION

Hereafter, the invention is described more particularly by way of its preferred embodiments with reference to the accompanying drawings.

Figure 1:
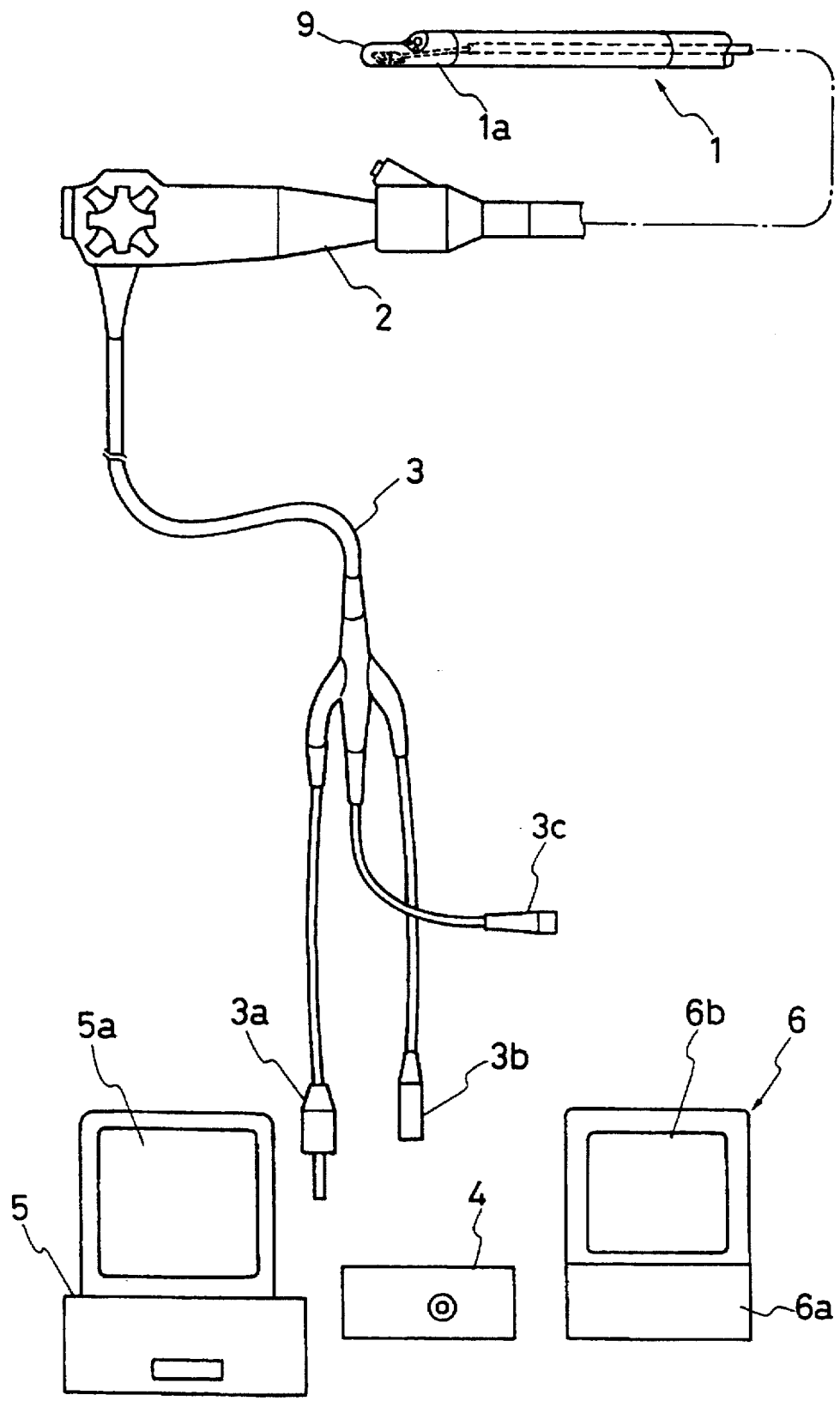
FIG. 1 is a schematic illustration of major component units of an endoscopic ultrasound examination system employing a dual ultrasound probe according to the present invention.

Shown in FIGS. 1 through 6 is a first embodiment of the invention, which is in the form of an endoscopic ultrasound examination system with a general configuration as illustrated in FIG. 1. More particularly, the endoscopic ultrasound examination system of FIG. 1 is provided with an ultrasound observation system along with an endoscopic observation system.

In these figures, indicated at 1 and 2 are an insertion tube and a manipulating head assembly of an ultrasound endoscope or an endoscopic ultrasound probe, respectively, and at 3 is a universal cable assembly which is divided into three separate cables at its proximal end, i.e., a cable with a light source connector 3a to be connected to a light source unit 4, a cable with an electric connector 3b to be connected to an endoscopic signal processor unit 5, and a cable with an ultrasound connector 3c to be connected to an ultrasound image observation unit 6. In this instance, the endoscopic signal processor 5 includes a monitor screen 5a to display endoscopic images thereon, and the ultrasound observation unit 6 includes an ultrasound signal processor 6a along with a monitor screen 6a for displaying ultrasound images thereon.

FIG. 2 shows in greater detail the construction of the above-mentioned insertion tube 1. As seen in this figure, an illumination window 7 and an observation window 8 of the endoscopic ultrasound probe are provided on an fore end portion 1a of the insertion tube 1, while a dome-like cap 10 is fitted in the fore end of the insertion tube 1, on the front side of the illumination and observation windows 7 and 8, to house an ultrasound transducer assembly 9 of the ultrasound observation system.

Figure 3:
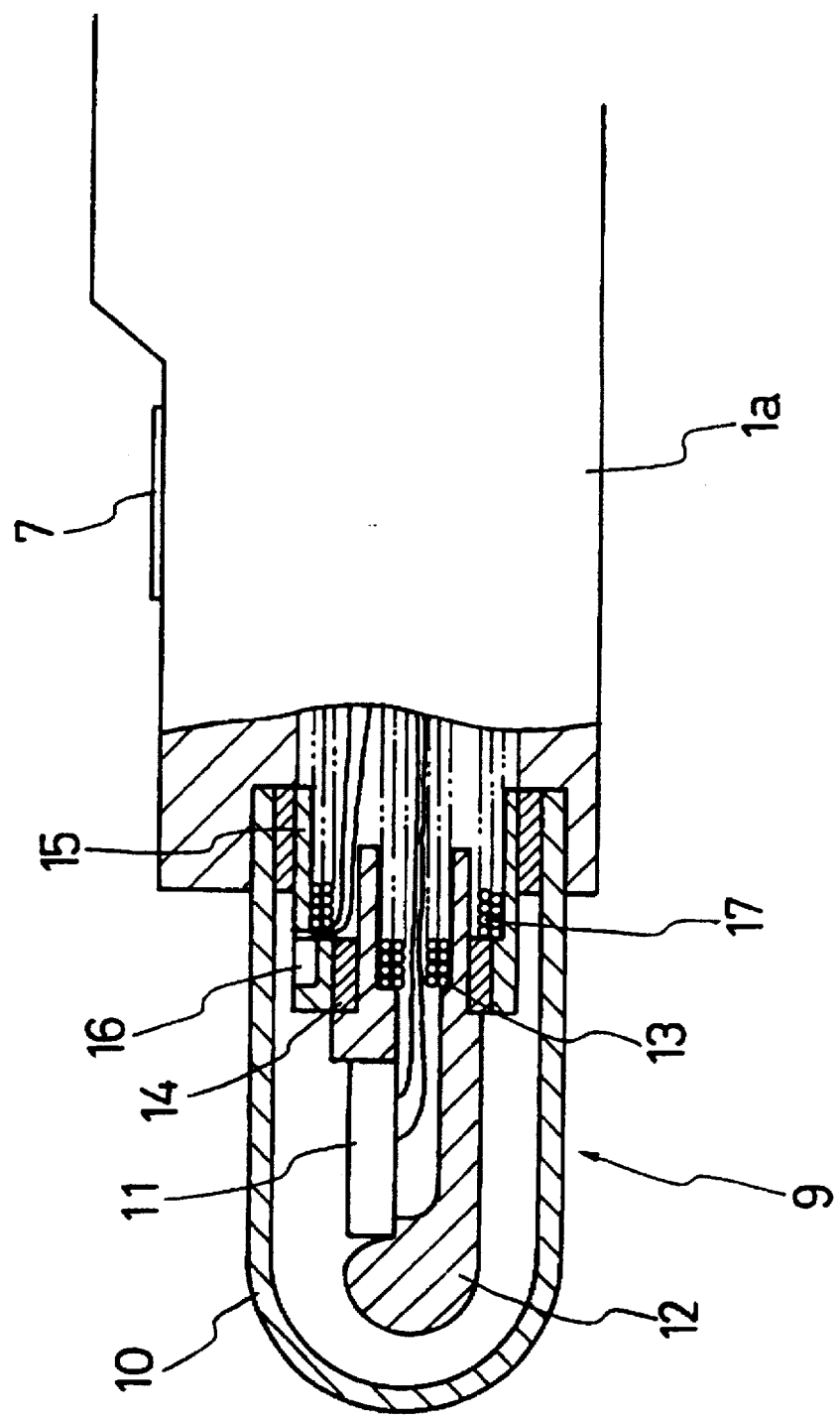
FIG. 3 is a schematic sectional view of a dual ultrasound transducer assembly housing cap at the distal end of the insertion tube.

As clear from FIG. 3 which shows the ultrasound transducer assembly 9 in a sectional view, the housing cap 10 is protruded from the fore end 1a of the insertion tube 1 as a protective cover for the ultrasound transducer assembly 9, which has a scanning ultrasound transducer element 11 mounted on a support member 12 for B-mode ultrasound scanning operations. The support member 12 is located at a center position within the cap 10, and connected at its base end to a first flexible rotation transmission shaft 13 which consists of a couple of tightly wound coils or the like. Upon rotationally driving the first flexible shaft 13 about its axis, the support member 12 is turned around to make a radial scan with the ultrasound transducer element 11 which is fixedly mounted on the support member 12.

Through a bearing 14, a support ring 15 is fitted around a base end portion of the support member 12 at a position clear of the active face of the scanning ultrasound transducer 11 on the support member 12. Provided on the outer periphery of the support ring 15 is a Doppler ultrasound transducer 16 for transmission and reception of Doppler ultrasound signals. Further, the support ring 15 is connected to a second flexible shaft 17 which is loosely and coaxially fitted on the first flexible shaft 13 to permit relative rotations of the two flexible shafts 13 and 17.

Figure 4:
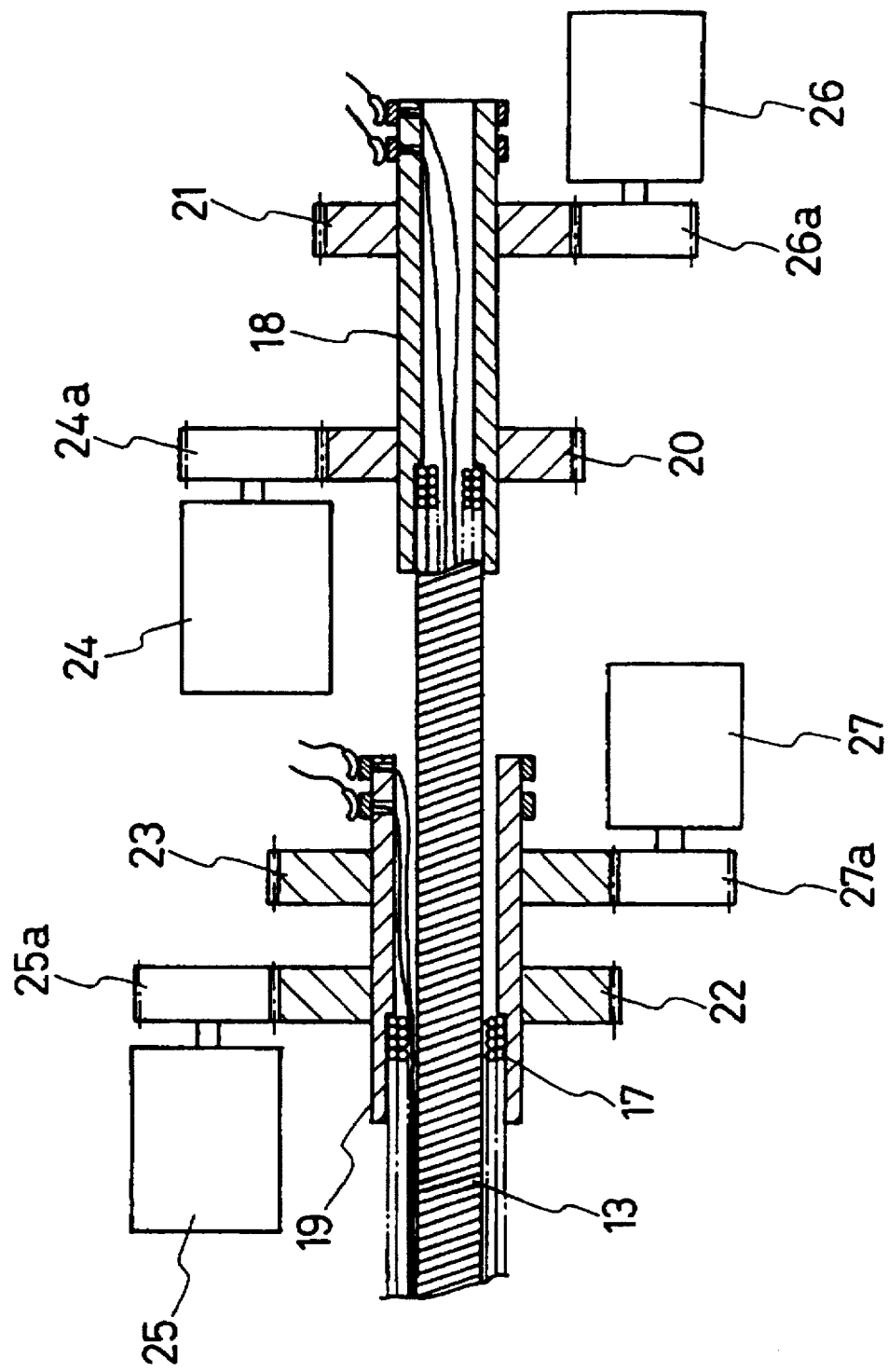
FIG. 4 is a partly cutaway schematic view of a dual ultrasound transducer drive mechanism.

As seen in FIG. 4, proximal ends of the first and second flexible shafts 13 and 17 are extended into the manipulating head assembly 2 of the ultrasound endoscope and connected to first and second relatively rotatable shafts 18 and 19, respectively. A pair of gears 20 and 21 are fixedly mounted on the first rotational shaft 18, while a pair of gears 22 and 23 are fixedly mounted on the second rotational shaft 19. The gears 20 and 22 on the first and second rotational shafts 18 and 19 are meshed with drive gears 24a and 25a which are coupled with drive motors 24 and 25, respectively. The other gears 21 and 23 are meshed with input gears 26a and 27a of encoders 26 and 27, respectively. Consequently, upon actuating the motor 24, the first rotational shaft 18 is rotated to turn the first flexible shaft 13 about its axis, and the scanning ultrasound transducer 11 on the support member 12 at the fore end of the first rotational shaft 18 is rotationally driven for a scanning operation in a predetermined direction. At this time, the rotational angle of the scanning ultrasound transducer 11 is detected by the encoder 26. On the other hand, upon actuating the motor 25, the second rotational shaft 19 is rotated to turn the second flexible shaft 17 about its axis, and as a result the support ring 15 at the fore end of the second flexible shaft 17 is rotated relative to the support member 12 to shift the position of observation of the Doppler ultrasound transducer 16 by a certain angle in the rotational direction. The angular position of the Doppler ultrasound transducer 16 in the rotational direction is detected by the encoder 27.

With the foregoing arrangements, firstly a B-mode ultrasound scan is carried out by rotationally driving the scanning ultrasound transducer 11 while transmitting ultrasound pulses and receiving return echoes through the scanning ultrasound transducer 11 at predetermined angular intervals. Received echo signals are transferred to the signal processor 6a of the ultrasound observation unit 6 to undergo predetermined signal processing operations, for generating video signals to display a B-mode tomographic ultrasound image of a scanned region on the monitor screen in the manner well known in the art. On the other hand, the Doppler ultrasound transducer 16 is so positioned and oriented as to transmit ultrasound pulses toward a specified or selected point of observation in the B-mode tomographic ultrasound image on display. The echo signals received through the Doppler transducer 16 are also transferred to the ultrasound signal processor 6a and thereby processed through predetermined signal processing operations to acquire in vivo motional data at the specified point of observation.

Figure 5:
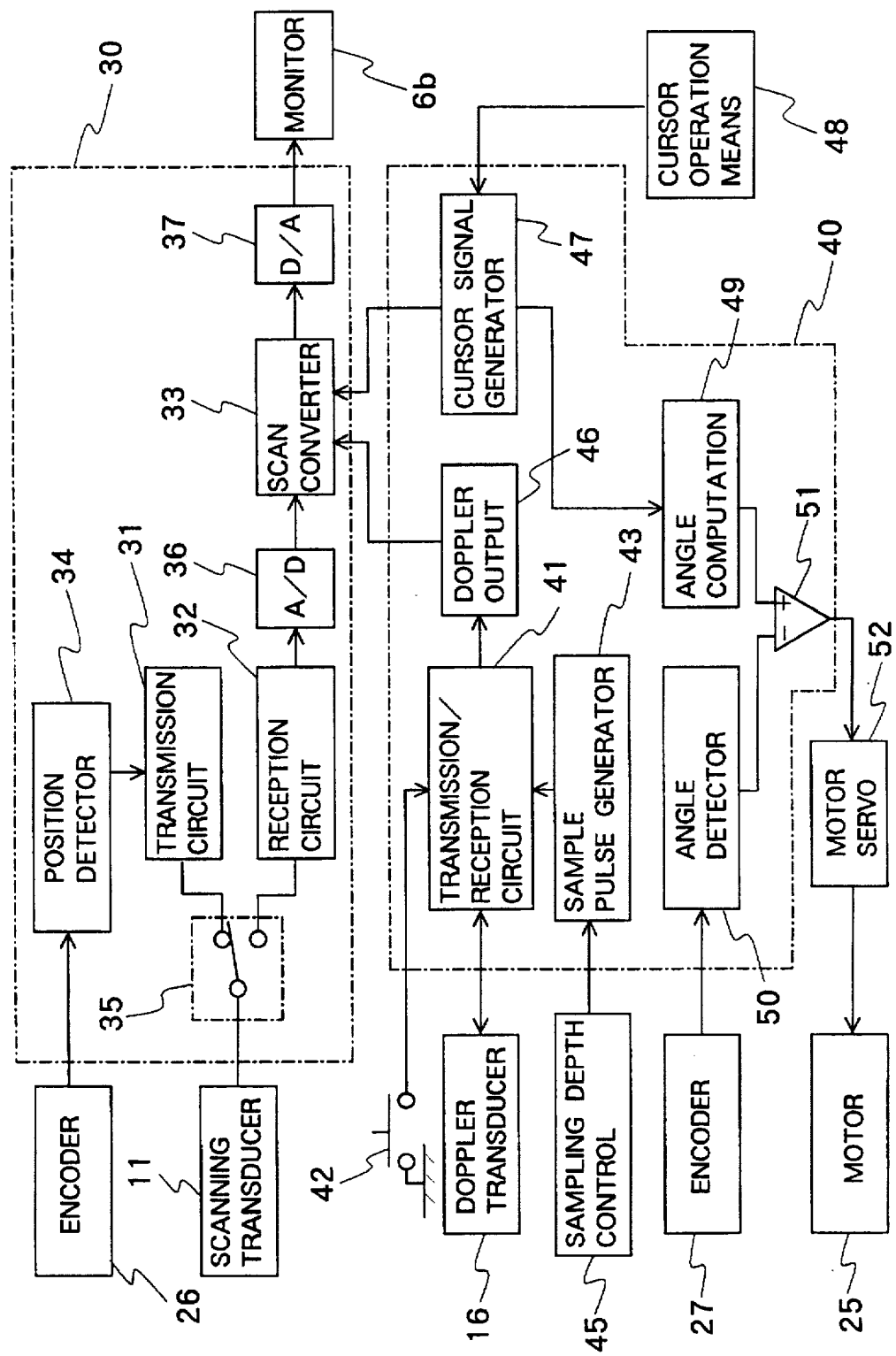
FIG. 5 is a block diagram of signal processing circuits of the ultrasound examination system.

FIG. 5 shows circuit arrangements of the above-described ultrasound signal processor 6a, which is largely constituted by a B-mode signal processor 30 and a Doppler signal processor 40. The B-mode signal processor 30 includes a signal transmission circuit 31, a signal reception circuit 32 and a scan converter 33. The signal transmission circuit 31 is connected to the afore-mentioned encoder 26 through a position detection circuit 34 to produce a transmission trigger signal at predetermined angular intervals during rotation of the scanning ultrasound transducer 11 on the basis angular position signals from the encoder 26.

Further, the signal transmission and reception circuits 31 and 32 are alternately connected to the scanning ultrasound transducer 11 through a switching means 35. More specifically, the signal transmission circuit 31 is firstly connected with the scanning ultrasound transducer 11 to transmit an ultrasound pulse signal toward an intracorporeal region of interest through the transducer at a time point when a trigger signal is sent out from the transmission circuit 31 on the basis of an angular position signal from the encoder 26. After transmission of an ultrasound pulse signal, the switching means 35 changes its position to connect the signal reception circuit 32 with the scanning ultrasound transducer 11 to receive return echo signals therefrom. Namely, the signal reception circuit 32 is supplied with return echo signals after conversion into electric signals, which are to be processed into video signals in the following stages. The electric signals of return echoes are fed to the scan converter 33, which is connected to the signal reception circuit 32 through a A/D converter 36, and sequentially stored in a memory of the scan converter 33 for each acoustic line. In this manner, ultrasound signals are transmitted and received at predetermined angular intervals during rotation of the scanning ultrasound transducer 11. As soon as a set of data by one scanning operation (one rotation) is collected in the memory of the scan converter 33, the memory contents are compiled to generate picture data for one frame of a radial tomographic ultrasound image, converted into analog video signals through D/A converter 37, and transferred to the monitor 6b to display a radial tomographic ultrasound image on its viewing screen in the usual manner.

On the other hand, the Doppler signal processor 40 includes a Doppler signal transmission/reception circuit 41 which is put in operation upon manipulating a Doppler operating switch 42 on. Connected to the Doppler signal transmission/reception circuit 41 is a sampling pulse generator circuit 43 which generates an ultrasound pulse signal for transmission through the Doppler ultrasound transducer 16 toward a target point of observation, as soon as a trigger signal is produced by the transmission/reception circuit 41 as a result of manipulation of the Doppler operating switch 42. Return echo signals are subjected to known signal processing operations at the transmission/reception circuit 41 to check for existence of blood flows or other vital motions at a specified spot in a B-mode tomographic ultrasound image which is displayed on the monitor screen.

The sampling pulse generator circuit 43 also has a function of controlling the depth of sampling position according to the position of the observation spot on the B-mode tomographic ultrasound image on display, by adjusting the sampling time point on the return echo signals into agreement with the depth of the target spot of observation. In this regard, a sampling position control means 45 in the form of a volume means or the like is provided thereby to control the sampling time point on received echo signals. Accordingly, by manipulating the sampling position control means 45, the sampling operation on return echo signals of a Doppler signal can be adjusted to a desired depth which corresponds to a target spot on the B-mode tomographic ultrasound image on the monitor screen.

A Doppler output circuit 46 which is connected to the transmission/reception circuit 41 is arranged either as a color Doppler output circuit or as a sound output circuit. In case a color Doppler signal is to be indicated on the monitor screen in overlapped relation with the tomographic ultrasound image, the output signal of the color Doppler output circuit 46 is supplied to the scan converter 33 of the B-mode signal processor 30 as indicated by a broken line in FIG. 5. In place of the above-described pulse Doppler observation, there may be employed the so-called continuous-wave Doppler observation using a couple of ultrasound transducers, one exclusively for transmission of a continuous ultrasound signal and the other exclusively for reception of return echoes. In case of continuous-wave Doppler observation, the sampling depth can be adjusted to a target spot through adjustment of the angle formed by the operational axes of the transmission and reception transducers.

As mentioned hereinbefore, the Doppler ultrasound transducer 16 is assembled into the ultrasound probe head casing to check for in vivo motional conditions exactly at a particular spot in a radial ultrasound image which is displayed on a monitor screen by operation of the B-mode ultrasound radial scanner. In this connection, the encoder 27 functions as a position detection mechanism to find the angular position of the Doppler ultrasound transducer 16 on the basis of a predetermined original point. Further, connected to the scan converter 33 is a cursor signal generator circuit 47 which is in turn connected to a cursor operating means 48 such as a mouse or the like. Accordingly, by way of the cursor operating means 48, the position for signal transmission and reception by the Doppler ultrasound transducer 16 can be shifted to a target position in line with an echoless blank spot on a B-mode tomographic ultrasound image which needs to be checked by the Doppler probe. The cursor signal generator circuit 47 is connected to an angle computing circuit 49 which functions to calculate the angle of the cursor position relative to its original point when the cursor is shifted to a certain position by operation of the cursor signal generator circuit 47.

The encoder 27 is connected to an angle detector 50 which produces a signal indicative of a current angular position of the Doppler transducer 16. At a comparator 51, the current position signal from the angle detector 50 is compared with a target angle signal which is received from the cursor signal generator circuit 47 through the angle computing circuit 49. On the basis of the result of this comparative measurement, an operating signal is sent to a motor servo circuit 52, which controls the operation of the motor 25, thereby applying a servo signal to the motor 25 to shift the Doppler transducer 16 into an angular position in line with a target point of observation in the direction of signal transmission and reception by the Doppler transducer 16.

The first embodiment of the invention, with the above-described construction, is operated in the manner as follows. Firstly, the insertion tube 1 of the ultrasound endoscope is introduced, for example, into an intracavitary portion to be examined. The introduction of the insertion tube 1 and surrounding conditions of intracavitary portions of interest can be monitored through the observation window of the endoscopic observation system. In case an intracavitary region which needs a B-mode ultrasound scan for examination or for a diagnostic purpose is spotted through the endoscopic observation system, the cap 10 which houses the dual ultrasound probe assembly 9 is located face to face with that particular region, and then the B-mode ultrasound scanner is actuated to put the scanning ultrasound transducer 11 in operation as described hereinbefore to obtain a tomographic ultrasound image of tissues in that region. For a B-mode radial scan, the scanning ultrasound transducer 11 is rotationally driven from the motor 24, and a resulting radial tomographic ultrasound image is displayed on the viewing screen of the monitor 6b as shown in FIG. 6.

In an ultrasound examination or diagnosis, it is a great advantage if one can get information on in vivo motional phenomena such as blood flows at a particular spot on a radial tomographic ultrasound image on display on the monitor screen 6b. For example, in some cases a diagnostic judgement can be given only after making a check as to whether an echoless blank spot in a B-mode ultrasound image is of a blood flow or of a diseased portion. Further, in case a blood flow through a cancer-affected region is detected, there are possibilities of cancer transfer in consideration of the location of the blood flow which could have conveyed cancer cells to other parts of the body. Therefore, from a diagnostic point of view, it is extremely important to check for blood flows in the vicinity of cancer cells. Furthermore, there may arise necessities for checking post-operative conditions of hardening treatments on esophageal varices. These checks can be made by the use of the above-described Doppler ultrasound observation means, which can be operated in relation with the B-mode ultrasound scanner to check for in vivo motional phenomena such as blood flows at a particular spot in a radial tomographic ultrasound image obtained by a B-mode scanning operation.

Figure 6:
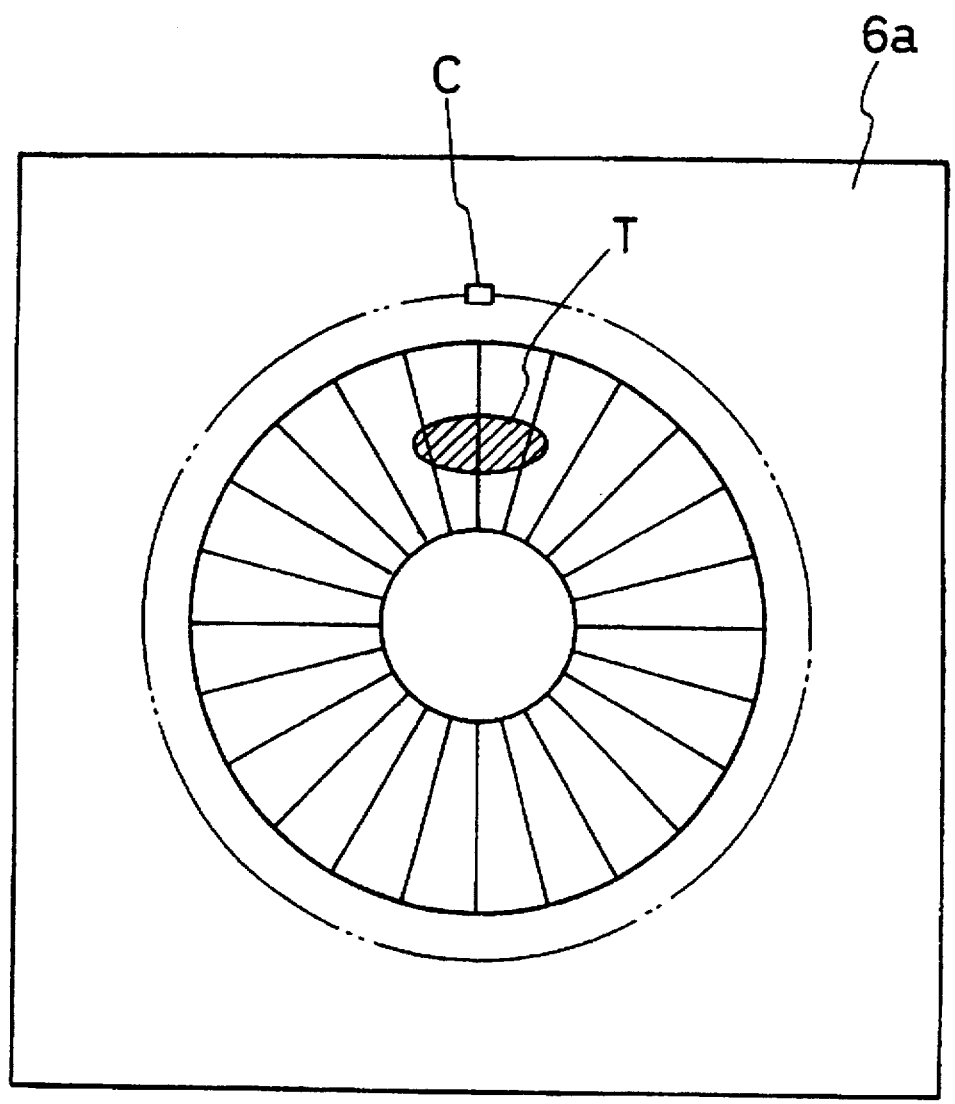
FIG. 6 is a schematic illustration of a monitor screen displaying a B-mode tomographic ultrasound image with an echoless blank spot.

For specifying a particular spot in a B-mode ultrasound image on display, as shown in FIG. 6, the cursor C is arranged to move along a predetermined locus of movement, which is indicated by an imaginary line in that figure, shifting its angular position in response to manipulation of the cursor operating means 48. Shown on the monitor 6b is a tomographic ultrasound image which contains a target spot T to be examined to check for in vivo motional conditions, particularly, to check for existence of a blood flow. The cursor C can be shifted to an angular position in line with the target spot T simply by manipulating the cursor operating means 48 while confirming its current position on the monitor screen. On the basis of the cursor position, the angle computing circuit 49 calculates the target angular position to which the Doppler ultrasound transducer 16 is to be moved, and the motor 25 is actuated to advance the Doppler ultrasound transducer 16 to the target angular position, which is indicated by the cursor C, in such a manner as to zeroize the angular differential from the current angular position of the Doppler transducer 16 which is detected by the angle detector 50 through the encoder 27. Then, the depth of the target spot T from the Doppler transducer 16 is measured to enter a suitable sampling position through the sampling position control means 45.

In this state, the Doppler operating switch 42 is turned on to actuate the Doppler ultrasound transducer 16, thereby transmitting an ultrasound pulse signal (or continuous wave signal) toward the target spot of observation while receiving and transferring return echoes to the transmission/reception circuit 41. The return echo signals are received at a position directionally in line with and to the depth of the target spot T, under control of the sampling position control circuit 43, so that, upon processing the received echo signals at the transmission/reception circuit 41, the operator can readily make a check for information on in vivo motions like blood flows at the target spot T in the B-mode tomographic ultrasound image on display. The results of the Doppler ultrasound examination can be indicated in a specific color on the monitor screen in the usual manner, or may be notified by a sound or other signals if desired. By so doing, the operator can be clearly notified of the results of examination.

Figure 7:
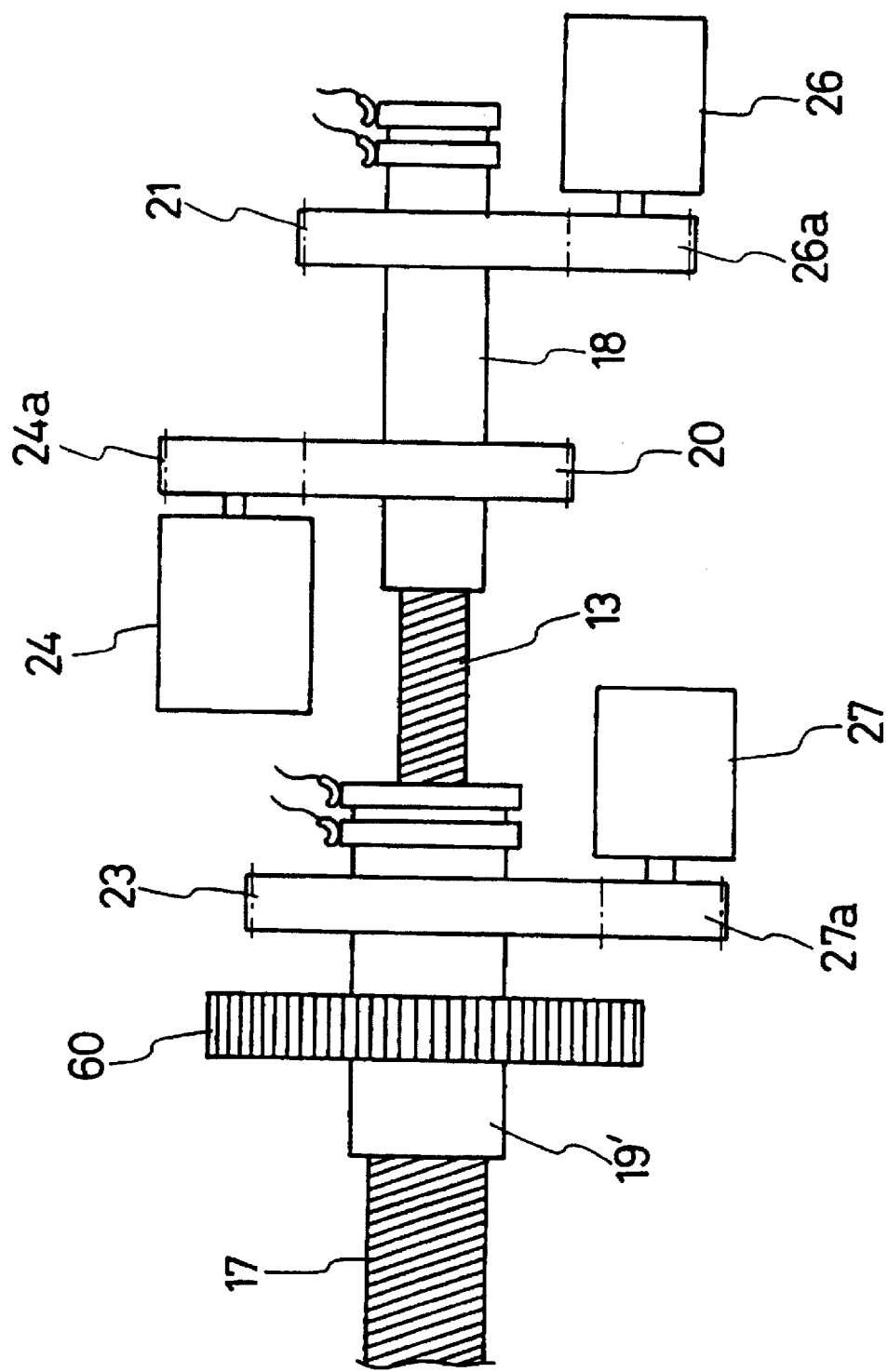
FIG. 7 is a schematic view of a dual ultrasound transducer drive mechanism in a second embodiment of the invention.
Figure 8:
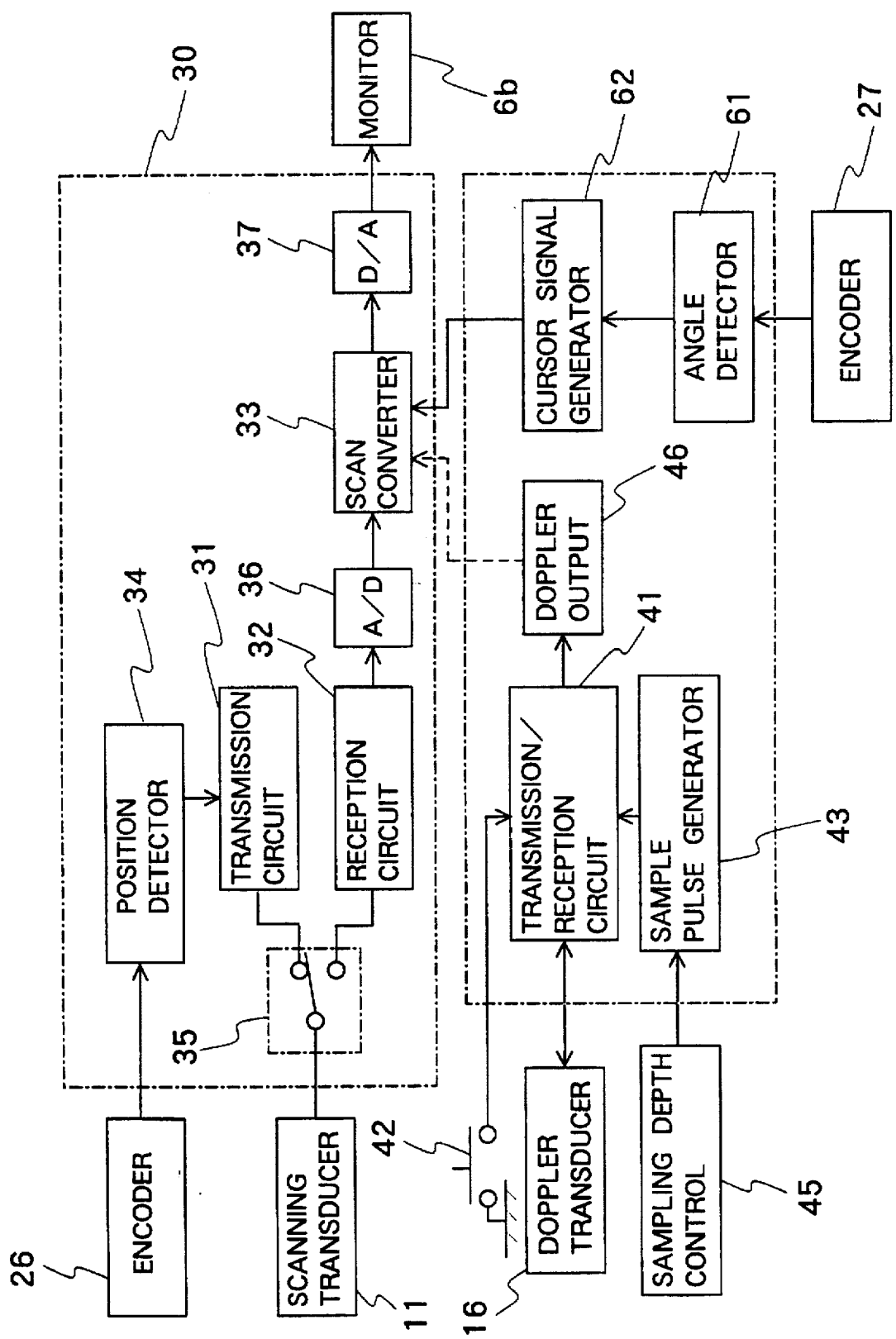
FIG. 8 is a block diagram of signal processing circuits in the second embodiment of the invention shown in FIG. 7.

Referring now to FIGS. 7 and 8, there is shown another embodiment of the invention, which is different from the foregoing first embodiment in that the Doppler ultrasound transducer 16 can be manually operated to shift its angular position. In the following description, those component parts which are common or equivalent with the counterparts in the first embodiments are simply designated by common reference numerals without repeating descriptions on them.

In this embodiment, as shown particularly in FIG. 7, instead of a gear which is coupled with a motor, the second rotational shaft 19' is connected to a manual rotating means 60. In order to detect the angular position of the Doppler ultrasound transducer 16, the rotational shaft 19' is also connected to the encoder 27. The output signal of the encoder 27 is likewise converted into an angular signal by the angle detector 51. In this case, however, in order to relate the angular position of the Doppler ultrasound transducer 16 directly with radial tomographic ultrasound images to be displayed on the monitor screen 6b, it is necessary to adjust the original point of the encoder 27 into agreement with that of the other encoder 26 which detects the angular position of the scanning ultrasound transducer 11. The angular signal of the angle detector 61 is fed to a cursor signal generator circuit 62, thereby to produce a signal of the current position of the Doppler transducer 16 to be put on the monitor screen 6b through the scan converter 33. Therefore, in order to move the Doppler transducer 16 into an angular position in line with an observation spot, it suffices for the operator to turn the manual rotating means 60 until the cursor C on the monitor screen 6b comes to a target angular position. Of course, the signal sampling position in the radial direction is adjustable to a suitable depth by way of the sampling position control means 45.

The second embodiment of FIGS. 7 and 8 can be operated in the same manner as the first embodiment in detecting a particular in vivo motional phenomena like blood flows at an echoless blank spot of a B-mode tomographic ultrasound image.

Although, as a typical example of B-mode ultrasound scanner, a radial ultrasound scanner is operatively combined with a Doppler ultrasound observation means in both of the foregoing embodiments of the invention, it is to be understood that a different type of B-mode ultrasound scanner can be similarly incorporated into the ultrasound probe head to obtain convincing information on in vivo motional phenomena like blood flows at a particular spot, for example, in a linear, sectoral or convex tomographic ultrasound image displayed on a monitor screen. A similar Doppler examination can be carried out on a particular spot of a B-mode tomographic ultrasound image which is obtained by an electronic scanning operation instead of the above-described mechanical scanning operation. Further, in place of the above-described ultrasound endoscope which has a dual ultrasound probe assembly on the front side of an endoscopic observation window, the ultrasound examination system according to the invention may be built into a catheter-like ultrasound probe designed to be introduced into an intracavitary portion through a biopsy channel of an endoscope or through a guide means other than a biopsy channel or into an external or extra-cutaneous ultrasound probe.

As clear from the foregoing description, the ultrasound examination system of the present invention employs, in combination with a B-mode ultrasound scanner, a Doppler ultrasound observation means which is operable to check for in vivo motions such as blood flows at a specified spot on a B-mode tomographic ultrasound image obtained by a scanning operation of the B-mode scanner. Accordingly, it becomes possible to obtain not only a tomographic image of tissues in an intracorporeal region of interest by a B-mode scan based on variations in acoustic impedance, but also information on in vivo motional conditions at a specific spot of the B-mode tomographic ultrasound image, contributing to enhance the accuracy of ultrasound examination and diagnosis to a significant degree.

What is claimed is:

1. A dual ultrasound probe for use in an ultrasound examination system, said dual ultrasound probe comprising:

a B-mode ultrasound transducer movable to perform a scan and having a predetermined scan range for a B-mode scan;

a Doppler ultrasound transducer movable substantially along the same locus as said B-mode scan;

a position detector means for detecting positions of said B-mode ultrasound transducer and Doppler ultrasound transducer within said scan range;

a signal processor for producing signals of a tomographic ultrasound image on the basis of ultrasound echo signals received through said B-mode ultrasound transducer and signals of B-mode ultrasound transducer position received from said position detector means;

a monitor having a viewing screen for displaying a B-mode ultrasound image on the basis of signals from said signal processor;

a cursor indicated on said viewing screen;

a cursor operating means for moving said cursor in predetermined directions on said viewing screen in relation with said B-mode ultrasound image to indicate a target position of Doppler examination;

an arithmetic processing means for calculating positional deviations of said Doppler ultrasound transducer from a cursor position; and a drive means for moving said Doppler ultrasound transducer into a position in line with said cursor position on the basis of a signal from said arithmetic processing means.

2. A dual ultrasound probe as defined in claim 1, further comprising a sampling pulse generator circuit for acquiring Doppler data at a target spot on an acoustic line of an ultrasound pulse signal transmitted by said Doppler ultrasound transducer after a shift to a position in line with said target position, and a sampling depth control means for controlling the Doppler pulse signal according to a depth of said target position.

3. A dual ultrasound probe as defined in claim 1, wherein said B-mode ultrasound transducer is of a radial scan type and said Doppler ultrasound transducer is rotationally driven to shift a position of Doppler examination in a rotational direction through a scan range of said B-mode ultrasound transducer.

* * * * *